(12) United States Patent
Miller et al.

(10) Patent No.: US 12,329,478 B2
(45) Date of Patent: Jun. 17, 2025

(54) SYSTEM AND METHOD FOR BREAKAWAY CLUTCHING IN AN ARTICULATED ARM

(71) Applicant: INTUITIVE SURGICAL OPERATIONS, INC., Sunnyvale, CA (US)

(72) Inventors: Daniel Miller, Fremont, CA (US); Nitish Swarup, Sunnyvale, CA (US); Michael Turner, Sunnyvale, CA (US); Arjang M. Hourtash, San Francisco, CA (US); Paul G. Griffiths, Santa Clara, CA (US); Paul W. Mohr, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/765,417

(22) Filed: Jul. 8, 2024

(65) Prior Publication Data
US 2024/0358456 A1 Oct. 31, 2024

Related U.S. Application Data

(63) Continuation of application No. 18/306,046, filed on Apr. 24, 2023, now Pat. No. 12,089,904, which is a
(Continued)

(51) Int. Cl.
*A61B 34/30* (2016.01)
*A61B 18/00* (2006.01)
(Continued)

(52) U.S. Cl.
CPC .............. *A61B 34/30* (2016.02); *B25J 9/1689* (2013.01); *B25J 9/1694* (2013.01); *B25J 13/085* (2013.01);
(Continued)

(58) Field of Classification Search
CPC .......... A61B 34/30; A61B 2018/00666; A61B 2018/00672; A61B 2018/00678;
(Continued)

(56) References Cited

U.S. PATENT DOCUMENTS

| 4,592,697 A | 6/1986 | Tuda et al. |
|---|---|---|
| 4,606,695 A | 8/1986 | Lenz |

(Continued)

FOREIGN PATENT DOCUMENTS

| CN | 102026783 A | 4/2011 |
|---|---|---|
| CN | 103097279 A | 5/2013 |

(Continued)

OTHER PUBLICATIONS

Office Action for Chinese Application No. CN202010742971.9, mailed Jul. 27, 2024, 32 pages.
(Continued)

*Primary Examiner* — Jaime Figueroa
(74) *Attorney, Agent, or Firm* — Artegis Law Group, LLP

(57) ABSTRACT

A system and method of breakaway clutching in a device includes a plurality of links coupled by a plurality of joints, a brake coupled to brake a first joint of the plurality of joints, and a control unit operatively coupled to the brake. The control unit includes one or more processors. The control unit switches the first joint from a first state of the first joint to a second state of the first joint in response to a determination that an external stimulus applied to the plurality of links or the plurality of joints meets at least a first criterion and switches the first joint from the second state to the first state in response to a speed associated with the first joint meeting at least a second criterion. The control unit causes more braking with the first brake in the first state than in the second state.

20 Claims, 3 Drawing Sheets

Related U.S. Application Data continuation of application No. 17/196,870, filed on Mar. 9, 2021, now Pat. No. 11,660,154, which is a continuation of application No. 16/563,342, filed on Sep. 6, 2019, now Pat. No. 10,973,596, which is a continuation of application No. 16/014,619, filed on Jun. 21, 2018, now Pat. No. 10,449,008, which is a continuation of application No. 15/126,996, filed as application No. PCT/US2015/021074 on Mar. 17, 2015, now Pat. No. 10,034,717.

(60) Provisional application No. 61/954,120, filed on Mar. 17, 2014.

(51) Int. Cl.
*A61B 34/00* (2016.01)
*B25J 9/16* (2006.01)
*B25J 13/08* (2006.01)
*A61B 90/00* (2016.01)

(52) U.S. Cl.
CPC ... *B25J 13/088* (2013.01); *A61B 2018/00666* (2013.01); *A61B 2018/00672* (2013.01); *A61B 2018/00678* (2013.01); *A61B 2034/305* (2016.02); *A61B 2090/035* (2016.02)

(58) Field of Classification Search
CPC ........ A61B 2034/305; A61B 2090/035; A61B 34/70; B25J 9/1689; B25J 9/1694; B25J 13/085; B25J 13/088
USPC ................. 700/245–264; 318/568.11–568.25
See application file for complete search history.

(56) References Cited

U.S. PATENT DOCUMENTS

| | | | |
|---|---|---|---|
| 4,693,665 A * | 9/1987 | Friederichs | B25J 9/142 |
| | | | 414/733 |
| 4,717,003 A | 1/1988 | McCormick et al. | |
| 4,848,546 A | 7/1989 | McCormick et al. | |
| 4,928,047 A * | 5/1990 | Arai | B25J 19/0004 |
| | | | 318/575 |
| 5,193,912 A | 3/1993 | Saunders | |
| 5,397,323 A * | 3/1995 | Taylor | A61B 34/71 |
| | | | 901/41 |
| 5,431,323 A | 7/1995 | Smith et al. | |
| 5,784,542 A * | 7/1998 | Ohm | A61B 34/35 |
| | | | 901/34 |
| 6,246,200 B1 | 6/2001 | Blumenkranz et al. | |
| 6,331,181 B1 | 12/2001 | Tierney et al. | |
| 6,377,011 B1 | 4/2002 | Ben-Ur | |
| 6,417,638 B1 | 7/2002 | Guy et al. | |
| 6,471,165 B2 * | 10/2002 | Twisselmann | F16M 11/24 |
| | | | 248/125.7 |
| 6,699,177 B1 | 3/2004 | Wang et al. | |
| 6,837,883 B2 | 1/2005 | Moll et al. | |
| 6,866,671 B2 | 3/2005 | Tierney et al. | |
| 7,048,745 B2 | 5/2006 | Tierney et al. | |
| 7,386,365 B2 | 6/2008 | Nixon | |
| 7,742,036 B2 | 6/2010 | Grant et al. | |
| 8,004,229 B2 | 8/2011 | Nowlin et al. | |
| 8,096,459 B2 | 1/2012 | Ortiz et al. | |
| 8,374,724 B2 | 2/2013 | Wieland et al. | |
| 8,401,702 B2 | 3/2013 | Okazaki et al. | |
| 8,541,970 B2 | 9/2013 | Nowlin et al. | |
| 8,573,461 B2 | 11/2013 | Shelton, IV et al. | |
| 8,624,537 B2 | 1/2014 | Nowlin et al. | |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 8,955,732 B2 | 2/2015 | Zemlok et al. | |
| 8,960,519 B2 | 2/2015 | Whitman et al. | |
| 9,028,468 B2 | 5/2015 | Scarfogliero et al. | |
| 9,265,584 B2 | 2/2016 | Itkowitz et al. | |
| 9,415,510 B2 | 8/2016 | Hourtash et al. | |
| 9,452,020 B2 | 9/2016 | Griffiths et al. | |
| 9,868,209 B2 | 1/2018 | Gomi et al. | |
| 10,034,717 B2 | 7/2018 | Miller et al. | |
| 10,206,752 B2 | 2/2019 | Hares et al. | |
| 10,299,821 B2 | 5/2019 | Shelton, IV et al. | |
| 10,449,008 B2 | 10/2019 | Miller et al. | |
| 10,973,596 B2 | 4/2021 | Miller et al. | |
| 11,660,154 B2 | 5/2023 | Miller et al. | |
| 2001/0031975 A1 | 10/2001 | Whitman et al. | |
| 2002/0049454 A1 | 4/2002 | Whitman et al. | |
| 2002/0120363 A1 | 8/2002 | Salisbury et al. | |
| 2003/0060927 A1 | 3/2003 | Gerbi et al. | |
| 2003/0192758 A1 * | 10/2003 | Murata | B25J 9/1674 |
| | | | 188/382 |
| 2004/0039485 A1 | 2/2004 | Niemeyer et al. | |
| 2004/0111081 A1 | 6/2004 | Whitman et al. | |
| 2004/0193146 A1 | 9/2004 | Lee et al. | |
| 2007/0055304 A1 | 3/2007 | Whitman | |
| 2007/0156122 A1 | 7/2007 | Cooper | |
| 2008/0046122 A1 | 2/2008 | Manzo et al. | |
| 2008/0114494 A1 | 5/2008 | Nixon | |
| 2008/0255608 A1 | 10/2008 | Hinman et al. | |
| 2008/0312687 A1 | 12/2008 | Blier | |
| 2009/0088774 A1 | 4/2009 | Swarup et al. | |
| 2009/0088775 A1 | 4/2009 | Swarup et al. | |
| 2009/0101692 A1 | 4/2009 | Whitman et al. | |
| 2009/0326322 A1 | 12/2009 | Diolaiti | |
| 2010/0204713 A1 * | 8/2010 | Ruiz Morales | B25J 9/041 |
| | | | 606/130 |
| 2011/0006101 A1 | 1/2011 | Hall et al. | |
| 2011/0006103 A1 | 1/2011 | Laurent et al. | |
| 2011/0011915 A1 | 1/2011 | Shelton, IV | |
| 2011/0022032 A1 | 1/2011 | Zemlok et al. | |
| 2011/0082462 A1 | 4/2011 | Suarez et al. | |
| 2011/0082587 A1 | 4/2011 | Ziaei et al. | |
| 2011/0155784 A1 | 6/2011 | Shelton, IV et al. | |
| 2011/0288573 A1 | 11/2011 | Yates et al. | |
| 2012/0006880 A1 | 1/2012 | Whitman et al. | |
| 2012/0043367 A1 | 2/2012 | Blier | |
| 2012/0083801 A1 | 4/2012 | Nixon | |
| 2012/0150154 A1 | 6/2012 | Brisson et al. | |
| 2012/0209314 A1 | 8/2012 | Weir et al. | |
| 2012/0211542 A1 | 8/2012 | Racenet | |
| 2012/0310256 A1 | 12/2012 | Brisson | |
| 2013/0032369 A1 | 2/2013 | Dridger | |
| 2013/0110130 A1 | 5/2013 | Manzo et al. | |
| 2013/0112730 A1 | 5/2013 | Whitman et al. | |
| 2013/0205558 A1 | 8/2013 | Sporer et al. | |
| 2013/0253533 A1 | 9/2013 | Bartol et al. | |
| 2014/0005718 A1 | 1/2014 | Shelton, IV et al. | |
| 2014/0052153 A1 | 2/2014 | Griffiths et al. | |
| 2014/0200596 A1 | 7/2014 | Weir et al. | |
| 2014/0200851 A1 | 7/2014 | Weir et al. | |
| 2015/0032126 A1 | 1/2015 | Nowlin et al. | |
| 2015/0051733 A1 | 2/2015 | Nowlin et al. | |
| 2015/0257840 A1 | 9/2015 | Mohr et al. | |
| 2016/0081753 A1 | 3/2016 | Kostrzewski | |
| 2016/0081754 A1 | 3/2016 | Kostrzewski et al. | |
| 2017/0202592 A1 | 7/2017 | Shelton, IV et al. | |
| 2017/0202594 A1 | 7/2017 | Shelton, IV et al. | |
| 2017/0202605 A1 | 7/2017 | Shelton, IV et al. | |
| 2018/0132850 A1 | 5/2018 | Leimbach et al. | |
| 2020/0253675 A1 | 8/2020 | Itkowitz et al. | |
| 2021/0077210 A1 | 3/2021 | Itkowitz et al. | |
| 2023/0255704 A1 | 8/2023 | Miller et al. | |

FOREIGN PATENT DOCUMENTS

| | | |
|---|---|---|
| DE | 102011004371 A1 | 8/2012 |
| EP | 1559380 A2 | 8/2005 |
| EP | 2438881 A1 | 4/2012 |
| JP | S6080892 U | 6/1985 |
| JP | H11253456 A | 9/1999 |
| JP | 2005125056 A | 5/2005 |
| JP | 2012000199 A | 1/2012 |

(56) References Cited

FOREIGN PATENT DOCUMENTS

| | | | |
|---|---|---|---|
| JP | 2013163232 A | | 8/2013 |
| JP | 2015502767 A | | 1/2015 |
| WO | WO-2006079108 | A1 | 7/2006 |
| WO | WO-2006124390 | A2 | 11/2006 |
| WO | WO-2007111737 | A2 | 10/2007 |
| WO | WO-2010016210 | A1 | 2/2010 |
| WO | WO-2012027581 | A2 | 3/2012 |
| WO | WO-2012035324 | A1 | 3/2012 |
| WO | WO-2012166510 | A1 | 12/2012 |
| WO | WO-2013045645 | A1 | 4/2013 |
| WO | WO-2013136583 | A1 | 9/2013 |
| WO | WO-2013181507 | A1 | 12/2013 |
| WO | WO-2015142930 | A1 | 9/2015 |

OTHER PUBLICATIONS

Dickert S.M., "Development of High Bandwidth Torque Sensor For Control of High Performance Manipulators," Mar. 1999, 28 pages.

Extended European Search Report for Application No. 14737996.0, mailed on Aug. 1, 2016, 10 pages.

Extended European Search Report for Application No. 15764121.8, mailed on Aug. 25, 2017, 10 pages.

Extended European Search Report for Application No. EP20161333.8 mailed on Jun. 17, 2020, 9 pages.

Extended European Search Report for Application No. EP23191917.6, mailed on Oct. 26, 2023, 08 pages.

International Search Report and Written Opinion for Application No. PCT/US15/21074, mailed on Jul. 17, 2015. 20 pages.

International Search Report and Written Opinion for Application No. PCT/US201 4/011 446, mailed on May 14, 2014, 14 pages.

Office Action for Chinese Application No. CN202010742971.9, mailed Nov. 29, 2023, 43 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

SYSTEM AND METHOD FOR BREAKAWAY CLUTCHING IN AN ARTICULATED ARM

RELATED APPLICATIONS

The present application is a continuation of U.S. patent application Ser. No. 18/306,046 filed Apr. 24, 2023, which is a continuation of U.S. patent application Ser. No. 17/196,870 filed Mar. 9, 2021, and now U.S. Pat. No. 11,660,154, which is a continuation of U.S. patent application Ser. No. 16/563,342, filed Sep. 6, 2019 and now U.S. Pat. No. 10,973,596, which is a continuation of U.S. patent application Ser. No. 16/014,619 filed Jun. 21, 2018 and now U.S. Pat. No. 10,449,008, which is a continuation of U.S. patent application Ser. No. 15/126,996 filed Sep. 16, 2016 and now U.S. Pat. No. 10,034,717, which is the U.S. national phase of International Application No. PCT/US2015/021074 filed Mar. 17, 2015, which designated the U.S. and claims priority to U.S. Provisional Patent Application No. 61/954,120 entitled "System and Method for Breakaway Clutching in an Articulated Arm" filed Mar. 17, 2014, the entire contents of each of which are herein incorporated by reference.

TECHNICAL FIELD

The present disclosure relates generally to operation of devices with articulated arms and more particularly to breakaway clutching of the articulated arms.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. Before these articulated arms and their end effectors may be used, they are typically moved to or near a desired working position and orientation. This movement may be performed by teleoperation or remote operation using one or more user input controls. As the complexity of these electronic devices increases and the articulated arms include large numbers of degrees of freedom, movement into the desired working position and orientation by teleoperation may become complex and/or time consuming. To streamline this operation, some articulated arms include a clutched or float state where one or more of the brakes and/or the actuators on the joints of articulated arms are released, allowing an operator to manually change the positions and/or the orientations of the articulated arms via direct manipulation. In this way the articulated arms may be quickly and easily positioned and/or oriented as desired. The clutch or float state is often engaged by manually activating one or more clutch controls on the articulated arm and/or selecting the clutch or float state at an operator console. This type of manual activation may be inconvenient and/or imprudent.

Accordingly, improved methods and systems for clutching articulated arms is desirable.

SUMMARY

Consistent with some embodiments, a computer-assisted medical device includes an articulated arm having one or more first joints and a control unit coupled to the articulated arm and having one or more processors. The control unit operates each of the first joints in multiple states. The multiple states include a locked state, wherein movement of respective first joints is restricted, and a float state, wherein movement of the respective first joints is permitted. The control unit further switches one or more second joints selected from the first joints from the locked state to the float state when a stimulus on the second joints exceeds one or more unlock thresholds and switches the second joints from the float state to the locked state when a velocity of each of the second joints is below one or more lock thresholds.

Consistent with some embodiments, a method of controlling motion in a medical device includes operating each of one or more first joints of an articulated arm of the medical device in one of multiple states. The multiple states include a locked state, wherein movement of respective joints is restricted, and a float state, wherein movement of the respective joints is permitted. The method further includes determining a stimulus on one or more second joints selected from the joints, switching the second joints from the locked state to the float state when the stimulus exceeds one or more unlock thresholds, determining a velocity of each of the second joints, and switching the second joints from the float state to the locked state when the velocity of each of the second joints is below one or more lock thresholds.

Consistent with some embodiments, a non-transitory machine-readable medium comprising a plurality of machine-readable instructions which when executed by one or more processors associated with a medical device are adapted to cause the one or more processors to perform a method. The method includes operating each of one or more first joints of an articulated arm of the medical device in one of multiple states. The multiple states include a locked state, wherein movement of respective joints is restricted, and a float state, wherein movement of the respective joints is permitted. The method further includes determining a stimulus on one or more second joints selected from the first joints, switching the second joints from the locked state to the float state when the stimulus exceeds one or more unlock thresholds, determining a velocity of each of the second joints, and switching the second joints from the float state to the locked state when the velocity of each of the second joints is below one or more lock thresholds.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
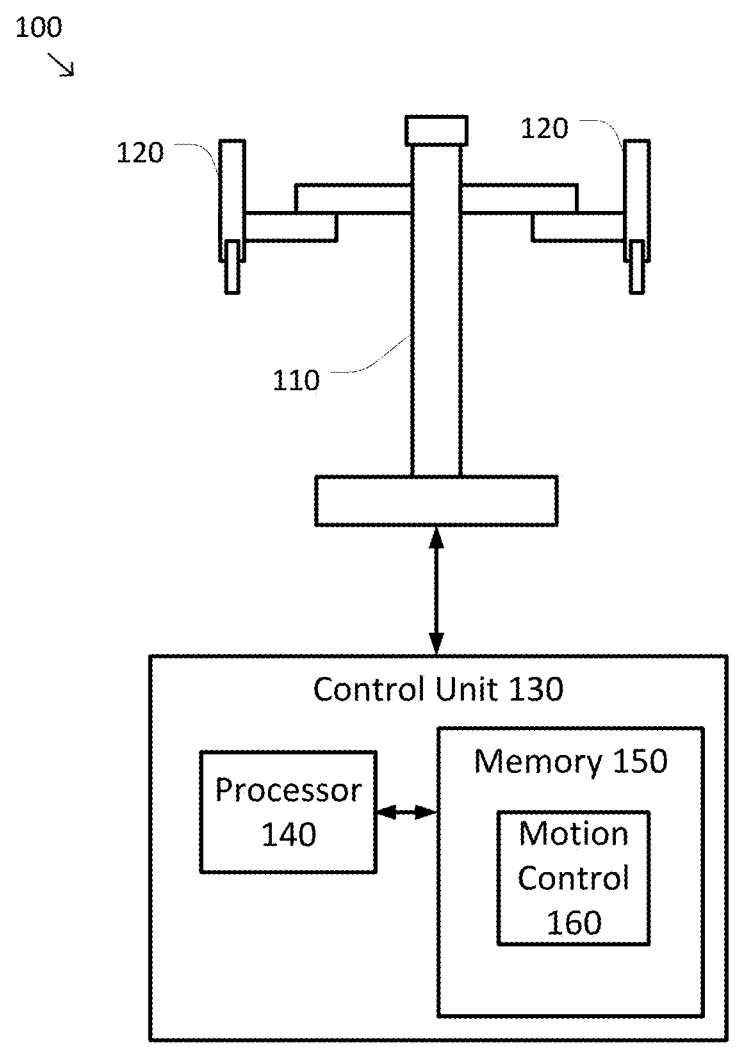
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 may support one or more end effectors. In some examples, device 110 may be consistent with a computer-assisted surgical device. The one or more articulated arms 120 each provide support for surgical instruments, imaging devices, and/or the like. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may be used with computer-assisted system 100.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Figure 2:
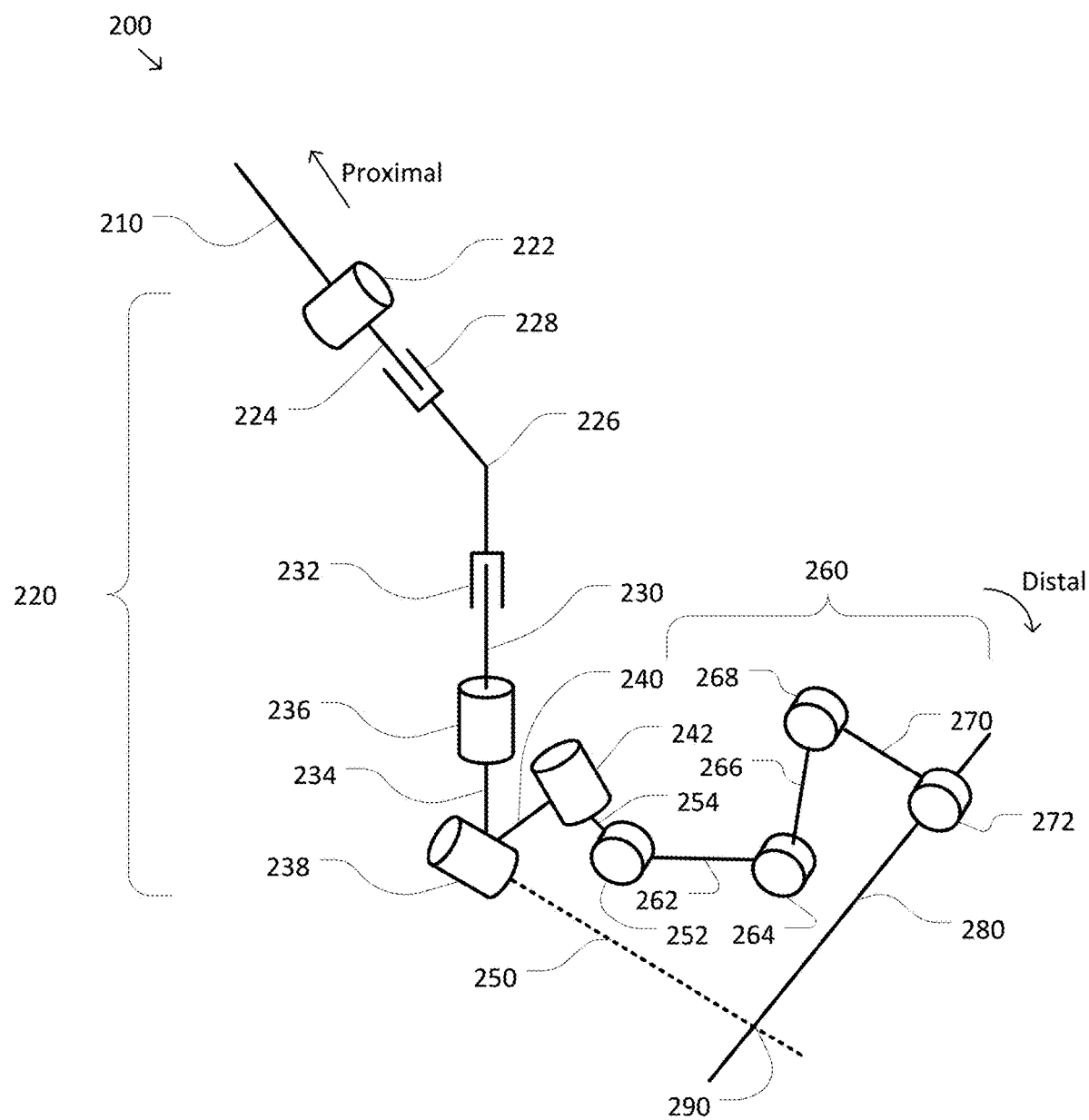
FIG. 2 is a simplified diagram showing an articulated arm according to some embodiments.

FIG. 2 is a simplified diagram showing an articulated arm 200 according to some embodiments. For example, the articulated arm 200 may be a portion of one of the articulated arms 120 in device 110. As shown in FIG. 2, the articulated arm 200 includes various links and joints. At the most proximal end of the articulated arm 200 is coupled to a platform 210. In some examples, platform 210 may be at a distal end of additional joints and links (not shown) from a computer-assisted device. Coupled to platform 210 is a series of set-up joints and links 220. The set-up joints and links 220 is rotationally coupled to platform 210 via a first set-up linkage joint 222. In some examples, additional set-up links and joints for other articulated arms (not shown) may be rotationally coupled to platform 210 using additional first set-up linkage joints. Coupled to the first set-up linkage joint 222 is a set-up base linkage 224 that is coupled to a proximal end of a set-up linkage extension link 226 via a first set-up linkage prismatic joint 228. A distal end of the set-up linkage extension link 226 is coupled to a proximal end of a set-up linkage vertical link 230 via a second set-up linkage prismatic joint 232. A distal end of the set-up linkage vertical link 230 is rotationally coupled to a proximal end of a support link 234 via a second set-up linkage joint 236. A first rotational joint 238 is coupled to a distal end of the support link 234. The first rotational joint 238 provides rotational control over the additional links and joints located distal to the first rotational joint 238. In some examples, a central axis 250 of the first rotational joint 238 may be aligned with a remote center 290 that may be fixed in location during teleoperation of the articulated arm 200.

A coupling link 240 couples the first rotational joint 238 to a second rotational joint 242. The second rotational joint 240 is coupled to a yaw joint 252 via a yaw link 254. Coupled distal to the yaw joint 252 is a parallelogram pitch mechanism 260. At a proximal end of the parallelogram pitch mechanism 260 is a first pitch link 262 coupling the yaw joint 252 to a first pitch joint 264. A second pitch link 266 couples the first pitch joint 264 to a second pitch joint 268. A third pitch link 270 couples the second pitch joint 268 to a third pitch joint 272. An instrument carriage is coupled to the third pitch joint 272 and includes an instrument shaft 280. One or more end effectors may be coupled to a distal end of the instrument shaft 280. In some examples, the parallel pitch mechanism 260 may be controlled to maintain the instrument shaft 280 in alignment with the remote center 290.

As shown in FIG. 2, the articulated arm 200 includes numerous linkages 224, 226, 230, 234, 240, 254, 262, 266, 270, and 280 whose relative positions and/or orientations may be adjusted using numerous prismatic joints 228 and 232 as well as numerous rotational joints 222, 236, 238, 242, 262, 264, 268, and 272. Each of the prismatic and rotational joints may include one or more sensors for sensing position, rotation, movement, force, torque, and/or the like on the respective joints.

Depending upon the desired ability to control the articulated arm 200 each of the various joints may be non-actuated or actuated joints. In some examples, a non-actuated joint may not include any actuators so that it is not capable of motion via teleoperation and/or motion control commands from a control unit for the articulated arm 200. In some examples, the non-actuated joint may include a brake the permits the control unit to prevent and/or restrict motion in the non-actuated joint. In the examples, of FIG. 2, joints 228, 232, and/or 236 may be non-actuated joints. In some examples, an actuated joint may include one or more actuators that may control motion of the actuated joint via teleoperation and/or motion commands. In some examples, an actuated joint may further include a brake.

In some embodiments, to prevent unwanted movement the various joints and links in the articulated arm 200 may be placed in a locked state where each of the non-actuated joint brakes are activated and each of the actuated joint actuators are commanded to hold the actuated joints at a commanded position. In some examples, the locked state may additionally prevent unwanted motion due to gravity acting on the articulated arm 200. Although not shown in FIG. 2, the articulated arm 200 may include one or more clutch buttons or controls. In some examples, the clutch buttons may be located at various locations along the instrument carriage. In some examples, additional clutch controls may be activated via operator controls at an operator console. By activating one or more of the clutch buttons or controls, one or more joints of the articulated arm may be switched from the locked state to a clutched or float state in which at least some of the non-actuated joint brakes may be at least partially released and at least some of the of the actuated joint actuators may permit motion of the joint away from the commanded positions. For example, activation of a clutch button located on the articulated arm 200 may place the articulated arm 200 in the float state while other portions of the computer-assisted device coupled to the platform 210 remain in the locked state. While the joints of the articulated arm 200 are in the float state, an operator may manually position and/or orient the articulated arm 200 into a desired working position and orientation.

In some embodiments, manual activation of the clutching mechanisms of the articulated arm 200 may not always be practical and/or prudent. In some examples, location of the clutch buttons or controls may not be convenient for easy activation by an operator. In some examples, the operator may not have a free finger and/or hand to operate the clutch controls. In some examples, coordination of the clutch controls with another operator located at an operator console may not be possible and/or practical. In some examples, the operator may not be able to operate the clutch controls without breaking a sterile field established around portions of the articulated arm 200. Thus, it would be advantageous to have at least portions of the articulated arm 200 enter the float state without activation of a clutch control by an operator.

In some embodiments, movement of the articulated arm 200 may be desired without manual clutch activation. In some examples, inadvertent collisions may occur between the operator, a patient, and/or an object and one or more links and/or joints of the articulated arm 200. In some examples, these inadvertent collisions may result in injury to the operator, injury to the patient, damage to the object, and/or damage to the articulated arm 200 due to the rigid position and/or orientation being maintained by the articulated arm 200. In some examples, being able to detect an inadvertent collision and have the articulated arm 200 automatically enter the float state may reduce injury to the operator, injury to the patient, damage to the object, and/or damage to the articulated arm 200.

Figure 3:
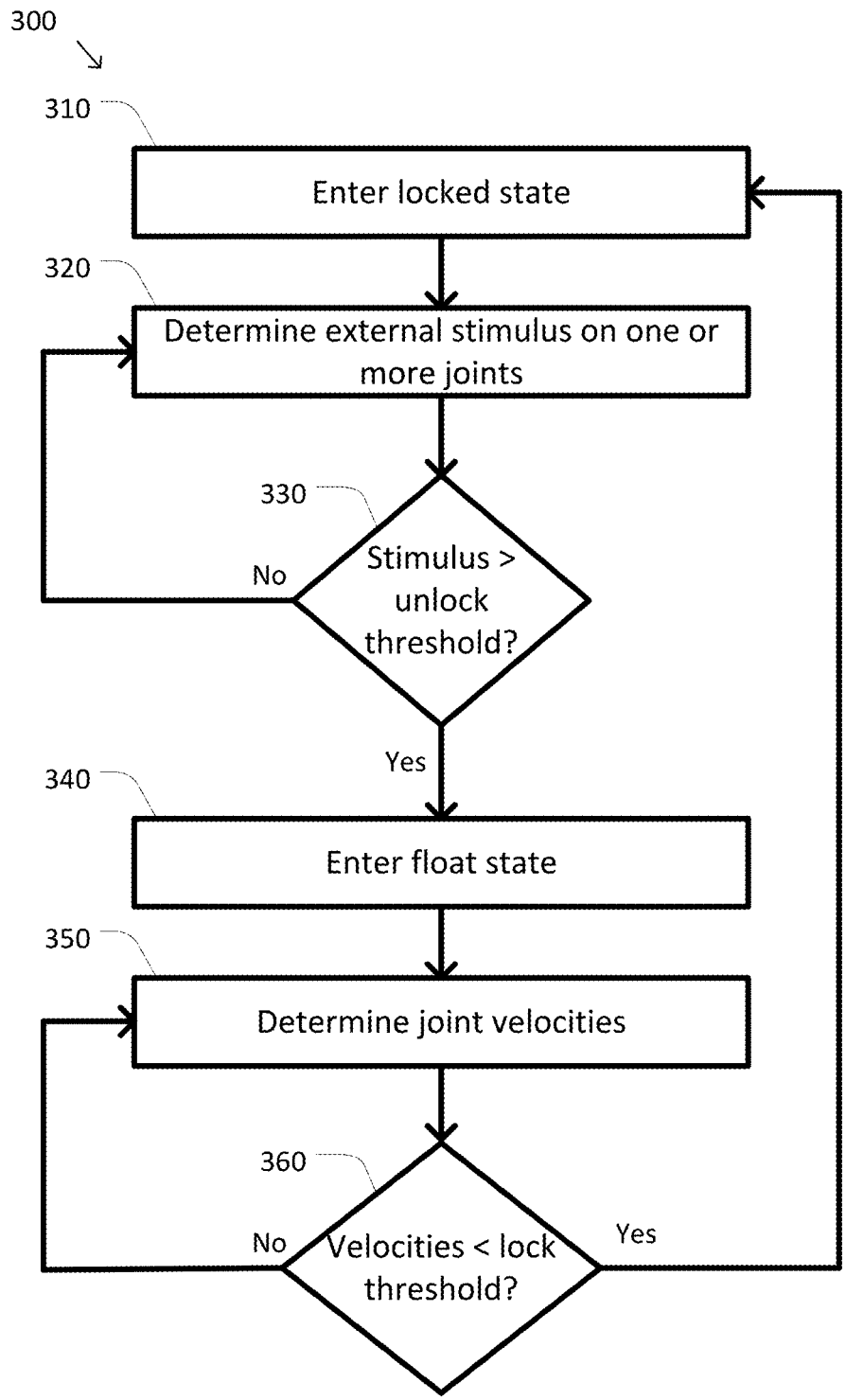
FIG. 3 is a simplified diagram of a method of breakaway clutching according to some embodiments.

FIG. 3 is a simplified diagram of a method 300 of breakaway clutching according to some embodiments. One or more of the processes 310-360 of method 300 may be implemented, at least in part, in the form of executable code stored on non-transient, tangible, machine readable media that when run by one or more processors (e.g., the processor 140 in control unit 130) may cause the one or more processors to perform one or more of the processes 310-360. In some embodiments, the method 300 may be performed by an application, such as motion control application 160.

At a process 310, a locked state is entered. Joints of an articulated arm, such as articulated arms 120 and/or 200 may be placed in the locked state by default. In the locked state, motion of the articulated arm may be prevented and/or reduced by activating brakes in each of the non-actuated joints of the articulated arm and holding each of the actuated joints of the articulated arm at a respective commanded position using corresponding actuated joint actuators.

At a process 320, external stimulus on one or more joints is determined. The one or more sensors associated with each of the joints of the articulated arm are periodically read and/or monitored to determine whether there is any external stimulus being applied to the one or more joints of the articulated arm. In some examples, linear sensors associated with prismatic joints and/or rotation sensors associated with rotational joints are monitored to determine actual positions of respective joints. In some examples, position errors may be determined based on differences between the actual positions and commanded positions in actuated joints and/or braked positions in non-actuated joints. In some examples, the position errors may be converted to approximate forces and/or torques on the respective joints by using one or more kinematic models, inverse Jacobian transposes, and/or control models for the respective joints. In some examples, the forces and/or torques on the respective joints may be measured using force and/or torque sensors, respectively, monitoring the respective joints. In some examples, joint velocities of the actuated joints may also be determined using one or more velocity sensors associated with actuated joints or numerically based on changes in the actual positions of the actuated joints.

At a process 330, it is determined whether the external stimulus on any of the joints exceeds an unlock threshold. The external stimulus values of each of the joints determined during process 320 is compared to one or more unlock thresholds to see whether any of the unlock thresholds are exceeded. In some examples, joints of the articulated arm may be switched to the float state using a process 340 when any one of the external joint stimulus values exceeds a respective unlock threshold. In some examples, joints of the articulated arm may be switched to the float state when a combination of two or more of the external joint stimulus values exceed respective unlock thresholds. In some examples, joints of the articulated arm may be switched to the float state when a weighted and/or un-weighted aggregation of external stimulus values from two or more joints exceeds a composite unlock threshold. In some examples, the aggregation may include an average, a median, a sum of squares, a minimum, a maximum, and/or like.

In some examples, each of the unlock thresholds for the respective joints may be different depending upon the location and/or purpose of the respective joints in the articulated arm. In some examples, the unlock thresholds may be adjusted based on a current pose, position, and/or orientation of the articulated arm. In some examples, the unlock threshold for a respective joint may be adjusted and/or disabled when the respective joint is beyond a soft stop near an end of possible motion for the respective joint. In some examples, the float state may be activated by default when the respective joint is beyond a soft stop. In some examples, determination of whether the external stimulus exceeds a threshold may be limited to a subset of the joints in the articulated arm. In some examples, external stimulus on non-actuated joints, which are braked, may not be monitored during process 320 and may not have corresponding unlock thresholds. In some examples, the unlock thresholds may be adjusted based on a size and/or a mass of the articulated arm. In some examples, the unlock thresholds may be large enough to avoid accidental switching to the float state due to gravitational forces and/or errors in the joint sensors.

In some examples, an unlock threshold may correspond to a threshold value associated with a position error between an actual position of a joint and a commanded and/or braked position of the joints. In some examples, the threshold value may be between 0.02 and 5 millimeters for a prismatic joint. In some examples, the threshold value may be between 0.03 and 0.5 degrees for a rotational joint. In some examples, one or more unlock thresholds may correspond to a force and/or torque being applied to the joint, either as measured and/or as determined during process 320. In some examples, the threshold value may be between 1 and 30 N for a force on a prismatic joint. In some examples, the threshold value may be between 1 and 30 N-m for a torque on a rotational joint. In some examples, the threshold value may exceed a force and/or torque saturation value for the joint.

In some embodiments, the unlock thresholds should be exceeded for a predetermined period of time before switching the articulated arm to the float state. In some examples, joints of the articulated arm may be switched to the float state when a respective external stimulus value exceeds a corresponding unlock threshold continuously for the predetermined period of time. In some examples, joints of the articulated arm may be switched to the float state when an aggregate, such as an average, of a respective external stimulus value over the predetermined period of time exceeds a respective stimulus value. In some examples, a sliding window and/or exponential smoothing may be used to determine the aggregate. In some examples, a filter may be used on the sensed external stimulus which puts an emphasis on mid-frequencies in order to better isolate disturbances due to human intention from disturbances due to gravity and other environmental factors which may be at low frequencies. In some examples, the mid-frequencies may extend from approximately 0.01 Hz to 10 Hz. In some examples, a discrete wavelet transform may be used in place of or combined with a filter to better isolate disturbances due to human intention. In some examples, the predetermined period of time may be set by an operator. In some examples, the predetermined period of time may be between 50 and 150 milliseconds. In some examples, the predetermined period of time may be different a first time breakaway clutching is activated, to avoid accidental switching to the float state due to residual momentum in the articulated arm due to other recently completed motion and/or static disturbances from the environment being confused with user input. In some examples, the locked state should be established with the external stimulus below the unlock threshold for a predetermined period of time before the first time breakaway clutching is activated, to avoid accidental switching to the float state due to likely transient situations, such as when an articulated arm is undocked from a patient, an end effector is attached or removed from the articulated arm, and/or the like. In some examples, the predetermined time may be extended between an additional 100 and 250 milliseconds after breakaway clutching is enabled.

When the external stimulus does not exceed the one or more unlock thresholds, the external stimulus is determined again using process 320. When the external stimulus exceeds the one or more unlock thresholds, joints of the articulated arm are switched to the float state using process 340.

At the process 340, the float state is entered. One or more of the joints of the articulated arm are placed in a float state where free and/or mostly free movement of the joints is permitted. In some examples, the joints being placed in the float state may be a subset of the joints in the articulated arm. In some examples, this permits breakaway clutching to apply to those portions of the articulated arm subject to the external stimulus. In some examples, the brakes on each of the non-actuated joints being placed in the float state may be released allowing motion of each of the non-actuated joints. In some examples, each of the actuated joints being placed in the float state may be commanded to move to the actual positions determined during process 320 or while the actuated joints remain in the float state. In some examples, each of the actuated joints being placed in the float state may also be commanded to match the joint velocities determined during process 320 or while the actuated joints remain in the float state. In some examples, setting the command positions of a feedback controller of the actuated joints to the actual positions and/or the command velocities of the feedback controller to the actual joint velocities gives the impression that the actuated joints are moving freely, and when gravity compensation is also being applied, then also with the impression of apparent weightlessness.

In some embodiments, the movement of the joints in the float state may be subject to damping. To reduce and/or prevent unrestricted and/or wild movement of the articulated arm while in the float state, one or more of the joints placed in the float state may be subject to some form of damped motion. For example, it may not be desirable for an articulated arm subject to a strong external stimulus, such as a hard collision, to move away from the strong external stimulus without some limitation. Constraining the clutched movement may reduce the risks of injury and/or damage caused by a fast moving articulated arm. In some examples, the damped motion may be implemented on non-actuated joints by partially releasing the brakes so as to place a drag on movement of the non-actuated joints. In some examples, the brakes may be partially released by controlling one or more voltage, currents, duty cycles, and/or the like of signals used to control the brakes. In some examples, the damped motion may be implemented on actuated joints by commanding the actuated joints to move a portion of the distance behind the actual position based on direction of motion, by increasing a derivative constant in the feedback controller without significantly affecting its stability margins, and/or by introducing a backward current and/or voltage on the actuators of the actuated joints to emulate a resisting force and/or torque. In some examples, the damped motion may be implemented on actuated joints by commanding the velocities of the actuated joints to a value below the joint velocities determined during process 320 or while the actuated joints remain in the float state. In some examples, the damped motion may be adjusted to account for a current pose, position, and/or orientation of the articulated arm, a size and/or a mass of the articulated arm, and/or the like.

In some embodiments, one or more of the joints in the articulated arm that are not placed in the float state may be subject to compliant motion restrictions. In some examples, the joints not placed in the float state may be commanded in response to detected movements of the joints placed in the float state. In some examples, the joints not placed in the float state may be commanded to one or more positions and/or orientations. In the examples, of FIG. 2, one or more of the joints in the parallelogram pitch mechanism 260 may be commanded to maintain intersection of the instrument shaft 280 with the central axis 250 at the remote center 290.

At a process 350, joint velocities are determined. The one or more sensors associated with each of the joints of the articulated arm are periodically read and/or monitored to determine the velocities of each of the joints that are in the float state. In some examples, changes in linear and/or rotational position between two consecutive monitoring intervals are used to estimate the joint velocities. In some examples, numerical and/or other differentiation techniques may be used to determine the joint velocities from the sensed positions. In some examples, velocity sensors on the joints may be monitored.

At a process 360, it is determined whether the joint velocities drop below a lock threshold. During breakaway clutching, the joints of the articulated arm are kept in the float state as long as continued motion of the articulated arm is detected. The joint velocities determined during process 350 are compared to one or more lock thresholds to see whether any continuing motion is detected in the articulated arm. In some examples, each of the joint velocities may be compared to a corresponding lock threshold. When each of the joint velocities is below its corresponding lock threshold, lack of motion is detected and the joints of the articulated arm are switched to the locked state using process 310. In some examples, joints of the articulated arm may be switched to the locked state using process 310 when a weighted and/or un-weighted aggregation of joint velocities from each of the joints is below a composite lock threshold. In some examples, the aggregation may include an average, a median, a sum of squares, a minimum, a maximum, and/or like.

In some examples, each of the lock thresholds for respective joints may be different depending upon the location and/or purpose of the respective joints in the articulated arm. In some examples, the lock thresholds may be adjusted based on a current, pose position, and/or orientation of the articulated arm. In some examples, the lock threshold for a respective joint may be adjusted and/or disabled when the respective joint is beyond a soft stop near an end of possible motion for the respective joint. In some examples, the locked state may be activated by default when the respective joint is beyond a soft stop. In some examples, determination of whether the joint velocities are below the lock thresholds may be limited to a subset of the joints in the articulated arm. In some examples, the lock thresholds may be adjusted based on a size and/or a mass of the articulated arm. In some examples, the lock thresholds may be large enough to avoid accidental switching to the lock due to errors in the joint sensors.

In some examples, the lock threshold may be between 0.1 and 10 millimeters per second for a prismatic joint. In some examples, the threshold value may be between 0.25 and 10 degrees per second for a rotational joint.

In some embodiments, the joint velocities should remain below the lock thresholds for a predetermined period of time before switching the joints of the articulated arm to the locked state. In some examples, joints of the articulated arm may be switched to the locked state when the joint velocities are below a corresponding lock threshold continuously for the predetermined period of time. In some examples, joints of the articulated arm may be switch to the locked state when an aggregate, such as an average, of a respective joint velocity over the predetermined period of time is below a respective lock threshold. In some examples, a sliding window and/or exponential smoothing may be used to determine the aggregate. In some examples, the predetermined period of time may be set by an operator. In some examples, the predetermined period of time may be between 100 and 200 milliseconds.

When the joint velocities remain above the lock thresholds, the joint velocities are determined again using process 350. When the joint velocities are below the lock thresholds, the joints of the articulated arm are switched to the locked state using process 310.

As discussed above and further emphasized here, FIG. 3 is merely an example which should not unduly limit the scope of the claims. One of ordinary skill in the art would recognize many variations, alternatives, and modifications. According to some embodiments, the breakaway clutching of method 300 may be disabled during certain operating modes of the articulated arm. In some examples, breakaway clutching may be disabled when the articulated arm is in a hard locked state during storage and/or when a cart on which the articulated arm is mounted is being transported between locations. In some examples, breakaway clutching may be disabled when the articulated arm is in an actuated teleoperation mode and/or executing commanded motion, such as when docked to a patient. In some examples, disabling breakaway clutching during actuated operation may reduce the likelihood that manual interference and/or collision with the articulated arm will interfere with the teleoperation and/or commanded motion and thus reduce the further likelihood of damaging objects being manipulated and/or causing injury to a patient on which the articulated arm is being used. In some examples, breakaway clutching may be adjusted, forced, or disabled when any of the joints in the articulated arm is beyond a soft stop position.

Some examples of control units, such as control unit 130 may include non-transient, tangible, machine readable media that include executable code that when run by one or more processors (e.g., processor 140) may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A device comprising:
a plurality of links coupled by a plurality of joints;
a brake coupled to brake a first joint of the plurality of joints; and
a control unit operatively coupled to the brake, the control unit comprising one or more processors;
wherein the control unit:
switches the first joint from a first state of the first joint to a second state of the first joint in response to a determination that an external stimulus applied to the plurality of links or the plurality of joints meets at least a first criterion, wherein the control unit causes more braking with the first brake in the first state than in the second state; and
switches the first joint from the second state to the first state in response to a speed associated with the first joint meeting at least a second criterion.

2. The device of claim 1, wherein movement of the first joint is more restricted in the first state than in the second state due at least in part to the more braking with the first brake in the first state than in the second state.

3. The device of claim 1, wherein:
the device comprises an arm, the arm comprising the plurality of links coupled by the plurality of joints;
the device further comprises a sensor; and
the control unit further determines whether the external stimulus meets the first criterion based on at least a value determined from information received from the sensor, the value being selected from the group consisting of:
a position error in a joint of the plurality of joints;
a force applied to a joint of the plurality of joints; and
a torque applied to a joint of the plurality of joints.

4. The device of claim 1, wherein to cause more braking with the first brake in the first state than in the second state comprises, the control unit:
activates the first brake while the first joint is in the first state; and
at least partially releases the first brake while the first joint is in the second state.

5. The device of claim 1, wherein the first criterion comprises:
the external stimulus exceeding a stimulus threshold; or
the external stimulus exceeding the stimulus threshold continuously for a predetermined period of time.

6. The device of claim 1, wherein the second criterion comprises:
the speed associated with the first joint falling below a speed threshold; or
an aggregate of the speed associated with the first joint over a predetermined period of time is below the speed threshold; or
the speed associated with the first joint remaining below the speed threshold continuously for the predetermined period of time.

7. The device of claim 1, wherein the control unit further:
delays switching, for a predetermined period of time after the determination has been made, of the first joint from the first state to the second state.

8. The device of claim 1, wherein:
the device comprises an arm, the arm comprising the plurality of links coupled by the plurality of joints; and
the first criterion is based on one or more properties selected from the group consisting of:
a location of the first joint in the arm;
a location of a second joint in the arm;
an amount of error in a joint sensor associated with the first joint;
an amount of error in a joint sensor associated with a second joint;
whether the first joint is beyond a soft stop position near an end of possible motion for the first joint;
whether the second joint is beyond a soft stop position near an end of possible motion for the second joint;
whether the first joint is actuated or non-actuated;
whether the first joint is prismatic or rotational;
whether the second joint is actuated or non-actuated; and
whether the second joint is prismatic or rotational.

9. The device of claim 1, wherein:
the device comprises an arm, the arm comprising the plurality of links coupled by the plurality of joints; and
the second criterion is based on one or more properties selected from the group consisting of:
a location of the first joint in the arm;
an amount of error in a joint sensor associated with the first joint;
whether the first joint is beyond a soft stop position near an end of possible motion for the first joint; and
whether the first joint is prismatic or rotational.

10. The device of claim 1, wherein the control unit further controls, while the first joint is in the second state, the first joint to move to a commanded position based on a current actual position of the first joint, or the first joint to move with a commanded velocity based on a current actual velocity of the first joint.

11. The device of claim 1, wherein the control unit further:
prevents the switching of the first joint from the first state to the second state when the device is in a predetermined mode selected from the group consisting of: a transport mode, a teleoperation mode, a commanded motion mode, and a docked to a patient mode.

12. A method of controlling a device comprising a plurality of links coupled by a plurality of joints and a brake coupled to brake a first joint of the plurality of joints, the method comprising:
switching, using a control unit, the first joint from a first state of the first joint to a second state of the first joint in response to determining that an external stimulus applied to the plurality of links or the plurality of joints meets at least a first criterion, wherein there is more braking with the first brake in the first state than in second first state; and
switching, using the control unit, the first joint from the second state to the first state in response to a speed associated with the first joint meeting at least a second criterion.

13. The method of claim 12, wherein movement of the first joint is more restricted in the first state than in the second state due at least in part to the more braking with the first brake in the first state than in the second state.

14. The method of claim 12, further comprising:
receiving, by the control unit, information about the plurality of joints or the plurality of links;
wherein determining whether the external stimulus meets the first criterion comprises determining a value based on the received information, the value being selected from the group consisting of:

a position error in one of the plurality of joints;
a force applied to one of the plurality of joints; and
a torque applied to one of the plurality of joints.

15. The method of claim 12, wherein the first criterion comprises:
the external stimulus exceeding a stimulus threshold, or the external stimulus exceeding the stimulus threshold continuously for a predetermined period of time.

16. The method of claim 12, wherein the second criterion comprises:
the speed associated with the first joint falling below a speed threshold; or
an aggregate of the speed associated with the first joint over a predetermined period of time is below the speed threshold; or
the speed associated with the first joint remaining below the speed threshold continuously for the predetermined period of time.

17. The method of claim 12, further comprising:
delaying switching, for a predetermined period of time after the determination has been made, of the first joint from the first state to the second state.

18. A non-transitory machine-readable medium comprising a plurality of machine-readable instructions which, when executed by one or more processors associated with a device comprising a plurality of links coupled by a plurality of joints and a brake coupled to brake a first joint of the plurality of joints, are adapted to cause the one or more processors to perform a method comprising:
switching the first joint from a first state of the first joint to a second state of the first joint in response to determining that an external stimulus applied to the plurality of links or the plurality of joints meets at least a first criterion, wherein there is more braking with the first brake in the first state than in the second state; and
switching the first joint from the second state to the first state in response to a speed associated with the first joint meeting at least a second criterion.

19. The non-transitory machine-readable medium of claim 18, wherein the method further comprises:
receiving information about the plurality of joints or the plurality of links;
wherein determining whether the external stimulus meets the first criterion comprises determining a value based on the received information, the value being selected from the group consisting of:
a position error in one of the plurality of joints;
a force applied to one of the plurality of joints; and
a torque applied to one of the plurality of joints.

20. The non-transitory machine-readable medium of claim 18, wherein:
the first criterion comprises: the external stimulus exceeding a stimulus threshold, or the external stimulus exceeding the stimulus threshold continuously for a predetermined period of time; or
the second criterion comprises: the speed associated with the first joint falling below a speed threshold, or an aggregate of the speed associated with the first joint over a predetermined period of time is below the speed threshold, or the speed associated with the first joint remaining below the speed threshold continuously for the predetermined period of time.

* * * * *

UNITED STATES PATENT AND TRADEMARK OFFICE
CERTIFICATE OF CORRECTION

PATENT NO. : 12,329,478 B2  
APPLICATION NO. : 18/765417  
DATED : June 17, 2025  
INVENTOR(S) : Daniel Miller et al.

It is certified that error appears in the above-identified patent and that said Letters Patent is hereby corrected as shown below:

On the Title Page

Item (63) Related U.S. Application Data:
Please delete "Continuation of application No. 18/306,046, filed on Apr. 24, 2023, now Pat. No. 12,089,904, which is a continuation of application No. 17/196,870, filed on Mar. 9, 2021, now Pat. No. 11,660,154, which is a continuation of application No. 16/563,342, filed on Sep. 6, 2019, now Pat. No. 10,973,596, which is a continuation of application No. 16/014,619, filed on Jun. 21, 2018, now Pat. No. 10,449,008, which is a continuation of application No. 15/126,996, filed as application No. PCT/US2015/021074 on Mar. 17, 2015, now Pat. No. 10,034,717." and insert --Continuation of application No. 18/306,046, filed on Apr. 24, 2023, now Pat. No. 12,089,904, which is a continuation of application No. 17/196,870, filed on Mar. 9, 2021, now Pat. No. 11,660,154, which is a continuation of application No. 16/563,342, filed on Sep. 6, 2019, now Pat. No. 10,973,596, which is a continuation of application No. 16/014,619, filed on Jun. 21, 2018, now Pat. No. 10,449,008, which is a continuation of application No. 15/126,996, filed on Sep. 16, 2016, now Pat. No. 10,034,717, which is a 371 of application No. PCT/US2015/021074, filed on Mar. 17, 2015.--.

Signed and Sealed this  
Twenty-second Day of July, 2025

Coke Morgan Stewart  
*Acting Director of the United States Patent and Trademark Office*